United States Patent
Swisher et al.

(10) Patent No.: US 12,198,455 B2
(45) Date of Patent: *Jan. 14, 2025

(54) CONVOLUTIONAL LOCALIZATION NETWORKS FOR INTELLIGENT CAPTIONING OF MEDICAL IMAGES

(71) Applicant: KONINKLIJKE PHILIPS N.V., Eindhoven (NL)

(72) Inventors: Christine Menking Swisher, San Diego, CA (US); Sheikh Sadid Al Hasan, Cambridge, MA (US); Jonathan Rubin, Cambridge, MA (US); Cristhian Mauricio Potes Blandon, Salem, MA (US); Yuan Ling, Somerville, MA (US); Oladimeji Feyisetan Farri, Yorktown Heights, NY (US); Rithesh Sreenivasan, Bengaluru (IN)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/502,133

(22) Filed: Nov. 6, 2023

(65) Prior Publication Data
US 2024/0071110 A1 Feb. 29, 2024

Related U.S. Application Data

(63) Continuation of application No. 17/053,153, filed as application No. PCT/EP2019/061602 on May 7, 2019, now Pat. No. 11,836,997.
(Continued)

(51) Int. Cl.
*G06T 7/00* (2017.01)
*G06F 40/10* (2020.01)
(Continued)

(52) U.S. Cl.
CPC .............. *G06V 20/64* (2022.01); *G06F 40/10* (2020.01); *G06N 3/044* (2023.01); *G06N 3/045* (2023.01);
(Continued)

(58) Field of Classification Search
CPC ........ G16H 30/40; G16H 50/20; G06F 40/10; G06N 3/0445; G06N 3/0454; G06N 3/08;
(Continued)

(56) References Cited

U.S. PATENT DOCUMENTS 8,321,196 B2 11/2012 Hale et al.
9,767,557 B1 * 9/2017 Gulsun ............ G06V 30/19173
(Continued)

FOREIGN PATENT DOCUMENTS

WO 2015114485 A1 8/2015
WO 2017089360 A1 6/2017

OTHER PUBLICATIONS

Aggarwal, et al., "Role of Segmentation in Medical Imaging: A Comparative Study", International Journal of Computer Applications, vol. 29, No. 1, Sep. 2011, pp. 54-61.
(Continued)

*Primary Examiner* — Van D Huynh

(57) ABSTRACT

A method (100) for generating a textual description of a medical image, comprising: receiving (130) a medical image of an anatomical region, the image comprising one or more abnormalities; segmenting (140) the anatomical region in the received medical image from a remainder of the image; identifying (150) at least one of the one or more abnormalities in the segmented anatomical region; extracting (160) one or more features from the identified abnormality; generating (170), using the extracted features and a trained text generation model, a textual description of the identified abnormality; and reporting (180), via a user interface of the
(Continued)

system, the generated textual description of the identified abnormality.

21 Claims, 5 Drawing Sheets

Related U.S. Application Data

(60) Provisional application No. 62/668,317, filed on May 8, 2018.

(51) Int. Cl.
  *G06N 3/044* (2023.01)
  *G06N 3/045* (2023.01)
  *G06N 3/08* (2023.01)
  *G06T 7/11* (2017.01)
  *G06V 10/44* (2022.01)
  *G06V 10/82* (2022.01)
  *G06V 20/64* (2022.01)
  *G16H 30/40* (2018.01)
  *G16H 50/20* (2018.01)

(52) U.S. Cl.
  CPC .............. *G06N 3/08* (2013.01); *G06T 7/0012* (2013.01); *G06T 7/11* (2017.01); *G06V 10/454* (2022.01); *G06V 10/82* (2022.01); *G16H 30/40* (2018.01); *G16H 50/20* (2018.01); *G06T 2207/20081* (2013.01); *G06T 2207/20084* (2013.01); *G06T 2207/30004* (2013.01)

(58) Field of Classification Search
  CPC ............ G06T 7/0012; G06T 7/11; G06T 2207/20081; G06T 2207/20084; G06T 2207/30004; G06V 10/82; G06V 2201/031; G06V 10/454; G06V 20/64
  See application file for complete search history.

(56) References Cited

U.S. PATENT DOCUMENTS

| | | | | |
|---|---|---|---|---|
| 2002/0193687 A1* | 12/2002 | Vining | .................... | G06T 15/08 128/920 |
| 2006/0274928 A1* | 12/2006 | Collins | .................. | G16H 30/40 382/132 |
| 2007/0041647 A1* | 2/2007 | Florin | .................... | G16H 30/20 382/233 |
| 2011/0107270 A1* | 5/2011 | Wang | ..................... | G16H 20/40 703/11 |
| 2011/0182493 A1* | 7/2011 | Huber | .................... | G16H 30/40 715/764 |
| 2012/0130223 A1* | 5/2012 | Reicher | .................. | G16H 30/40 600/407 |
| 2012/0172700 A1* | 7/2012 | Krishnan | ............... | A61B 6/505 600/407 |
| 2015/0089337 A1* | 3/2015 | Grady | ................. | G06F 3/04845 715/202 |
| 2015/0261915 A1* | 9/2015 | Yanagida | .............. | G06F 40/169 382/131 |
| 2015/0262014 A1* | 9/2015 | Iwamura | ................ | G16H 50/20 382/128 |
| 2016/0314246 A1* | 10/2016 | Roberge | ................. | G16H 30/20 |
| 2017/0177795 A1* | 6/2017 | Mabotuwana | ......... | A61B 6/037 |
| 2018/0033144 A1 | 2/2018 | Risman et al. | | |
| 2018/0060533 A1* | 3/2018 | Reicher | .................. | G16H 10/60 |

OTHER PUBLICATIONS

Kisilev, et al., "Medical image captioning: learning to describe medical image findings using multi-task-loss CNN", Jan. 1, 2011, Computer Science, 8 pages.

Shin, et al., "Learning to Read Chest X-Rays: Recurrent Neural Cascade Model for Automated Image Annotation", 2016 IEEE Conference on Computer Vision and Pattern Recognition, pp. 2497-2506.

International Search Report and Written Opinion for International Application No. PCT/EP2019/061602, filed May 7, 2019, 15 pages.

Yu, et al., "Assembling Deep Neural Networks for Medical Compound Figure Detection", Information 2017, 8, 48, pp. 1-11.

Johnson, et al., "DenseCap: Fully Convolutional Localization Networks for Dense Captioning", Computer Science, Computer Vision and Pattern Recognition, submitted on Nov. 24, 2015, pp. 1-10.

Saad, et al., "Integration of Medical Ontology Concepts To Annotate Medical Images", Jurnal Teknologi, 77:29 (2015) pp. 27-34.

Przelaskowski, et al., "Computer-Aided Interpretation of Medical Images: Mammography Case Study", Machine Graphics and Vision, Jan. 2007, pp. 1-27.

Ypsilantis, et al., "Recurrent Convolutional Networks for Pulmonary Nodule Detection in CT Imaging", Machine Learning, Computer Vision and Pattern Recognition, submitted on Sep. 30, 2016, pp. 1-36.

Oberkampf, et al., "Interpreting Patient Data usng Medical Background Knowledge", Interpretation of Patient Data, pp. 1-5, Jul. 2012.

\* cited by examiner

CONVOLUTIONAL LOCALIZATION NETWORKS FOR INTELLIGENT CAPTIONING OF MEDICAL IMAGES

CROSS REFERENCE TO RELATED APPLICATIONS

This application is a Continuation application of U.S. application Ser. No. 17/053,153 filed Nov. 5, 2020, which is the U.S. National Phase application under 35 U.S.C. § 371 of International Application No. PCT/EP2019/061602 filed May 7, 2019, which claims the benefit of U.S. Provisional Patent Application No. 62/668,317 filed May 8, 2018. These applications are hereby incorporated by reference herein.

FIELD OF THE DISCLOSURE

The present disclosure is directed generally to methods and systems for automated generation of a textual description from a medical image.

BACKGROUND

Medical images are utilized for the diagnosis and treatment of a wide array of conditions and diseases, and constitute a significant percentage of all medical information. CT scans, MRIs, X-rays, and ultrasound images are just a few of the medical imaging techniques used for diagnosis and treatment. Typically, radiologists perform specific steps to acquire a medical image, interpret it, and then prepare a report for the clinician. As a result, the knowledge, skills, and experience of a radiologist all play a vital role in medical image interpretation. However, interpreting medical images and summarizing the information contained therein in a text format is an intensely time-consuming task that often represents a bottleneck in clinical diagnosis pipelines.

Automatically describing the content from an image is a key challenge in artificial intelligence at the intersection of computer vision and natural language processing. Automated methods and systems that efficiently and accurately describe image content would significantly improve diagnosis and/or treatment workflow, thereby lowering costs and improving patient care. Automated text generation to describe two-dimensional images has been disclosed. However, these approaches are typically not suitable for medical imaging as there are additional complexities that need to be learned by machine learning algorithms designed to do object recognition and other relevant tasks.

Additionally, the downsampling often used in natural images to reduce dimensionality (reducing dimensionality allows for faster training and requires less training data) often results in loss of clinically significant features. Indeed, going from a HDR to LDR (e.g. 16-bit to 8-bit image) destroys important image characteristics and reduces performance in computer vision tasks. This has a particularly strong impact in radiology and pathology, where images tend to have a higher dynamic range than natural images.

SUMMARY OF THE EMBODIMENTS

There is a continued need for automated systems and methods that can generate a textual description of a medical image, thereby eliminating bottlenecks and improving patient care.

The present disclosure is directed to inventive methods and systems for the automated generation of textual descriptions from three-dimensional medical images which are generated from various different imaging modalities. Various embodiments and implementations herein are directed to a textual description generation system that utilizes one or more classifiers to characterize a medical image. Upon receiving a three-dimensional medical image, the system segments an anatomical region, such as an organ, away from the remainder of the image. One or more abnormalities in the segmented anatomical region are then identified. The system extracts one or more features from the identified abnormality, and generates a textual description using the extracted features and a trained text generation model. The system reports the generated textual description of the identified abnormality to a user such as a technician or clinician.

Generally in one aspect, a method for generating a textual description of a medical image is provided. The method includes: (i) receiving a medical image of an anatomical region, the image comprising one or more abnormalities; (ii) segmenting the anatomical region in the received medical image from a remainder of the image; (iii) identifying at least one of the one or more abnormalities in the segmented anatomical region; (iv) extracting one or more features from the identified abnormality; (v) generating, using the extracted features and a trained text generation model, a textual description of the identified abnormality; and (vi) reporting, via a user interface of the system, the generated textual description of the identified abnormality.

According to an embodiment, the medical image is a three-dimensional image.

According to an embodiment, the step of identifying the abnormality in the segmented anatomical region further comprises localizing the identified abnormality in three-dimensional space.

According to an embodiment, the method further includes the step of combining generated textual description from two or more identified abnormalities into a single textual description.

According to an embodiment, the two or more extracted features are merged to generate a feature vector for the identified abnormality.

According to an embodiment, the method further includes the step of utilizing, by a clinician, the reported textual description for diagnosis or treatment.

According to an embodiment, the method further includes the step of training, using a training data set, the text generation model to generate a textual description from an identified abnormality.

According to an embodiment, the step of identifying at least one of the one or more abnormalities in the segmented anatomical region comprises a convolutional neural network and/or a long short-term memory (LSTM) network.

According to an embodiment, the step of generating a textual description of the identified abnormality comprises a long short-term memory (LSTM) network.

According to an aspect is a system for generating a textual description of a medical image. The system includes: (i) an image segmenting module configured to receive a medical image of an anatomical region, the image comprising one or more abnormalities, and further configured to segment the anatomical region in the received medical image from a remainder of the image; (ii) an abnormality identification module configured to identify at least one of the one or more abnormalities in the segmented anatomical region; (iii) a feature extraction module configured to extract one or more features from the identified abnormality; (iv) a text generation module configured to generate, using the extracted features and a trained text generation model, a textual description of the identified abnormality; and (v) a user interface configured to report the generated textual description.

According to an embodiment, the feature extraction module is configured to combine two or more extracted features to generate a feature vector for the identified abnormality.

According to an embodiment, the text generation module is configured to combine generated a generated textual description from two or more identified abnormalities into a single textual description.

According to an embodiment, the text generation module is configured to be trained, using a training data set, to generate a textual description from an identified abnormality.

According to an embodiment, the system comprises one or more of a convolutional neural network and a long short-term memory (LSTM) network.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the various embodiments discussed herein. The terms "program" or "computer program" are used herein in a generic sense to refer to any type of computer code (e.g., software or microcode) that can be employed to program one or more processors or controllers.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system for generating a textual description of a three-dimensional medical image. More generally, Applicant has recognized and appreciated that it would be beneficial to provide an automated system to interpret medical images. The system uses one or more classifiers to characterize a medical image. Upon receiving a three-dimensional medical image, the system segments an anatomical region, such as an organ, away from the remainder of the image. One or more abnormalities in the segmented anatomical region are then identified. The system extracts one or more features from the identified abnormality, and generates a textual description using the extracted features and a trained text generation model. The system reports the generated textual description of the identified abnormality to a user such as a technician or clinician via a user interface, where it can be utilized for patient care.

Figure 1:
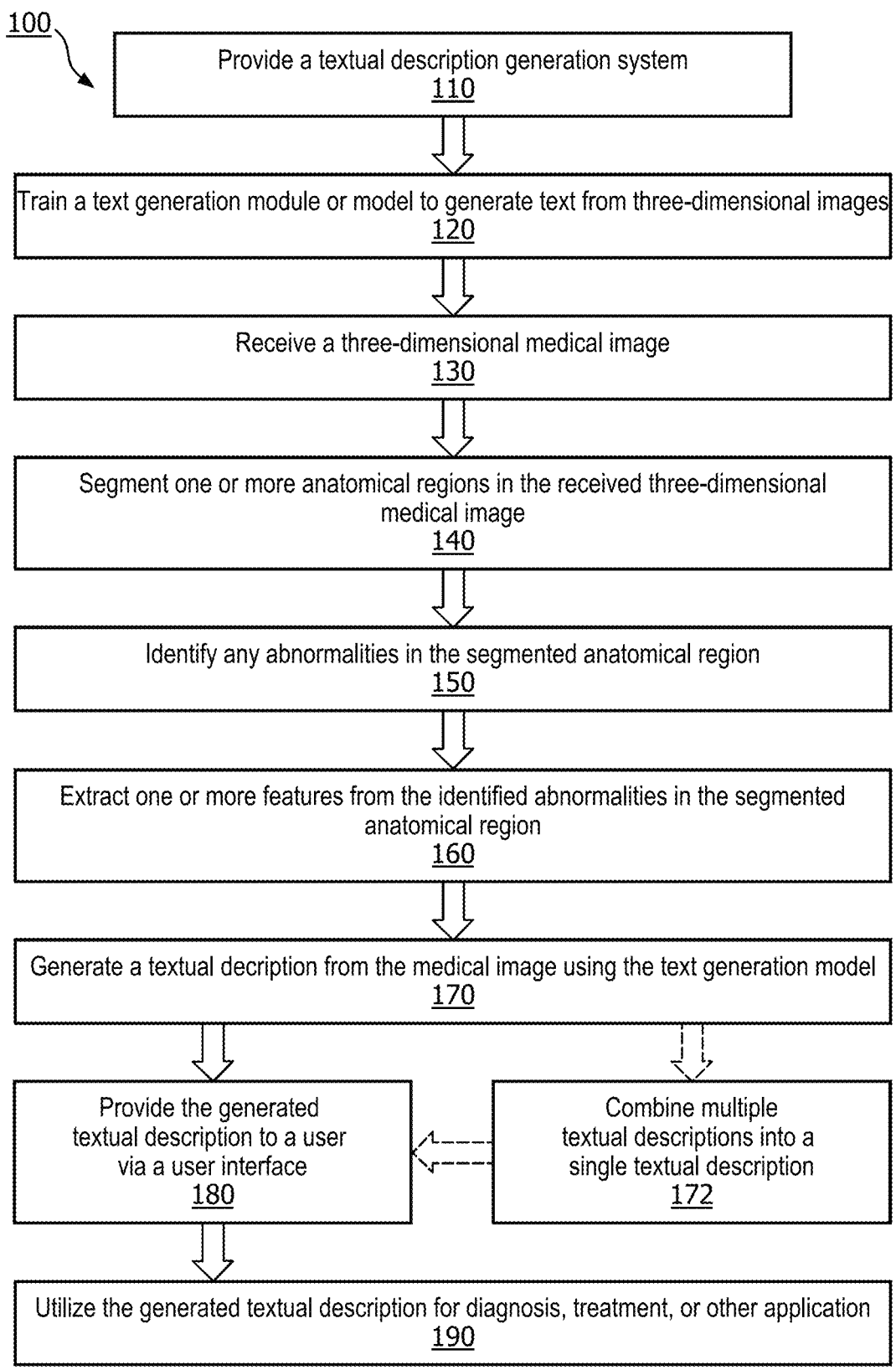
FIG. 1 is a flowchart of a method for generating a textual description of a medical image, in accordance with an embodiment.

Referring to FIG. 1, in one embodiment, is a flowchart of a method 100 for generating a textual description of a medical image. At step 110 of the method a textual description generation system is provided. The textual description generation system may be any of the systems described or otherwise envisioned herein. For example, the textual description generation system can comprise an image segmenting module, an abnormality identification module, a feature extraction module, a text generation module, and/or a user interface. Many other systems, modules, and components are possible.

At step 120 of the method, the system is trained to automatically generate text from identified abnormalities. According to an embodiment, a text generation module or model of the system is trained using a data set of known imaging associated with provided textual description. The text generation module or model may be trained using any method for training, including machine learning processes and methods. According to one embodiment, the text generation module or model is trained by a developer of the text generation system prior to implementation of the system in a clinical setting.

According to an embodiment, the text generation module or model is trained using descriptive sentences from medical literature in view of features extracted from associated medical images. For example, the approach may utilize an encoder-decoder neural network. Image features may be encoded into a fixed-length vector representation via a convolutional neural network (CNN), and then the representation may be decoded into a natural language description. The decoder can be a long short-term memory (LSTM) network which is trained as a language model conditioned on the image encoding.

According to an embodiment, during training of the text generation module or model, the image features can be provided as input to the first LSTM cell along with the first caption word, and an accompanying sequence of words can be similarly passed along to the subsequent LSTM cells. Thus, the image weights are shared across all the LSTM steps during the decoding stage to learn the association between image features and caption words. A GRU (Gated Recurrent Unit) can also be utilized in place of LSTM.

According to an embodiment, an attention mechanism can be utilized over the image features in the decoder such that the caption words can learn the inherent alignments for important image regions without explicitly relying on segmentation information. As an alternate embodiment based on the anatomy identified via DICOM tags or via an anatomy classification module, the system can further determine how many attention blocks are required. For example, a CT image of the abdomen may cover many organs such as liver, pancreas, stomach, small intestine, and/or large intestine, and the system can comprise an attention network for each organ. As another example, an MM of the brain can comprise many different regions and the system can comprise different attention networks for different lobes of the brain that can look across slices. Ultimately, the series of LSTM cells learns the probabilities of the next word given an input word and medical image such that the resulting model is able to generate a caption (phrase or sentence) when given a medical image.

According to an embodiment, the captions generated from different sequences of abnormal slices can be combined using a natural language processing module to form a single, cohesive report. For example, in an endoscopy report the slices identified in various regions of the gastrointestinal regions—such as the esophagus, stomach, and duodenum—presenting mucosal erosion abnormalities can be combined into a single caption such as "mucosal erosions seen at multiple locations of upper GI." The text generation module or model can therefore be trained to receive as input a series of captions, identify any correlation and co-reference between the captions with respect to abnormalities clinical natural language (NLP) tools such as MetaMap with UMLS terminologies to come up with meaningful captions.

At step 130 of the method, the system receives a three-dimensional medical image obtained using a first imaging modality. For example, the medical image may be obtained by CT scan, X-ray, MM, PET scan, ultrasound, and/or many other imaging modalities. Typically, the medical image will be provided in a digital format, or will be converted from an analog or other non-digital format to a digital format. The medical image may be obtained by the system directly, or may be provided to the system from an external source. For example, a facility or other clinical setting or network may comprise one or more text generation systems configured to receive medical images from a variety of different providers, internally and/or externally. Accordingly, the text generation system may receive X-rays from a first device or facility, and may receive MM images from a second device or facility. Alternatively, the text generation system may receive all medical images from the same device or facility. As another option, the text generation system may receive medical images that are uploaded or downloaded to the system or are otherwise directly provided by a clinician, technician, or other provider. The text generation system may receive a medical image directly from the modality by which the image is obtained, and thus the text generation system may comprise or be in communication with a wired and/or wireless communications network configured to receive these medical images.

At step 140 of the method, the system analyzes the received medical image to segment one or more anatomical regions in the received three-dimensional medical image from a remainder of the image. According to an embodiment, a segmentation model or module analyzes the received medical image to perform organ segmentation with adaptive thresholding. For example, the system can perform organ segmentation by adaptive thresholding with dilation to create a mask. The segmentation model or module may generate a graph of a slice or other portion of the three-dimensional image, which may typically be a two-dimensional representation. The segmentation model or module may then generate a graph or other thresholding representation of the image by analyzing one or more parameters of the image, such as intensity, color, shading, and other parameters or measurements. The segmentation model or module may utilize thresholding or other analysis parameters to identify an organ or other region of interest relative to background or areas not of interest.

Figure 2:
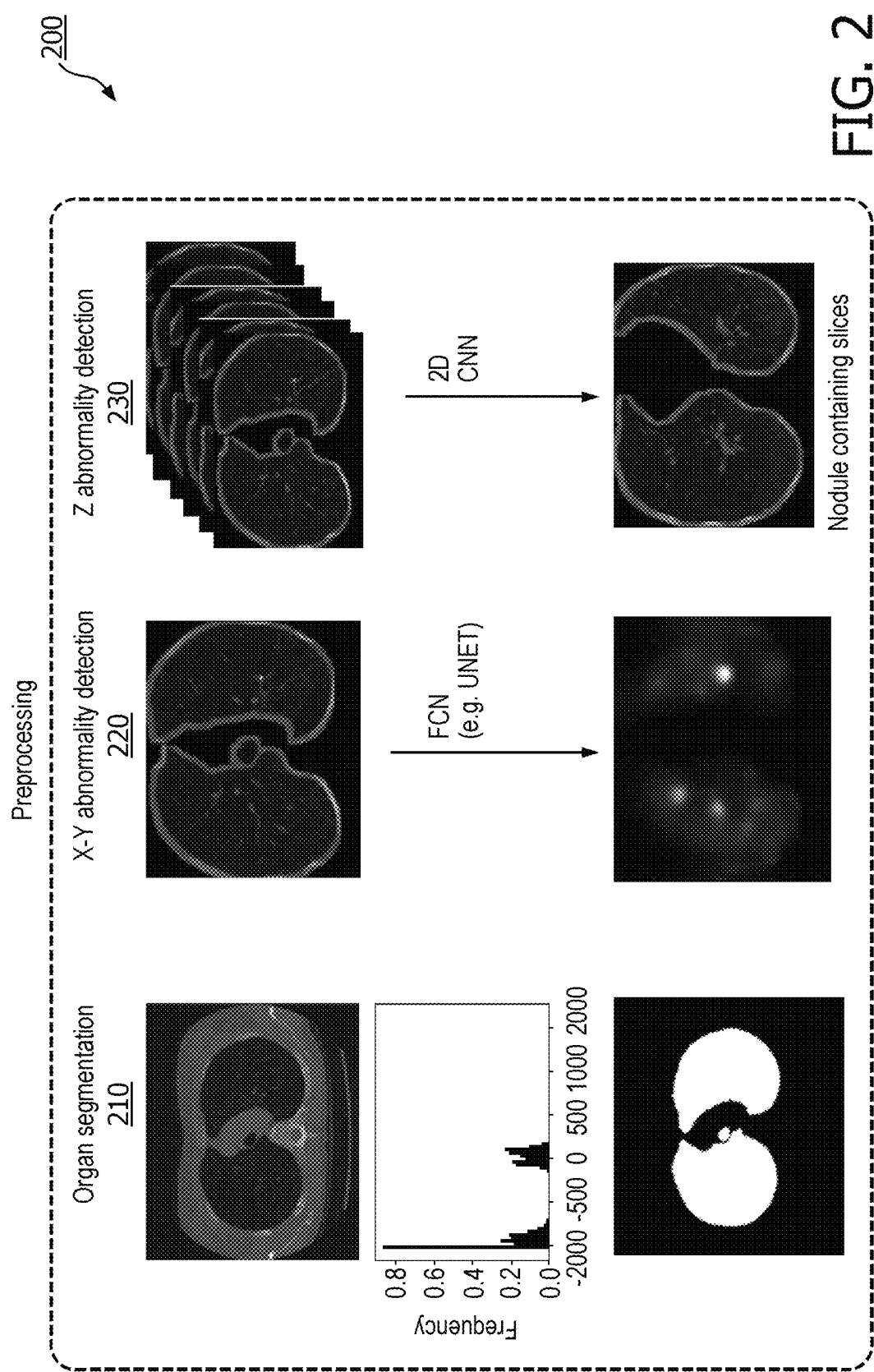
FIG. 2 is a schematic representation of a system or workflow for preprocessing of an image prior to text generation, in accordance with an embodiment.

Referring to FIG. 2, for example, is a schematic representation of a system or workflow 200 for preprocessing of an image prior to text generation, where preprocessing can comprise one or more steps. At 210, for example, a segmentation model or module analyzes the received medical image to perform organ segmentation with adaptive thresholding. The image is processed to produce a segmented organ representation which is utilized for abnormality detection in downstream steps of the method.

At step 150 of the method, the system analyzes the segmented one or more anatomical regions to identify an abnormality. As described or otherwise envisioned herein, the one or more anatomical regions may be analyzed by an abnormality module or model configured or trained to identify an abnormality in a segmented organ or region of interest. According to an embodiment, the abnormality module or model uses a fully convolutional neural network (FCN), such as U-Net, followed by 3D characterization by a LSTM. Other methods for abnormality detection are possible. Notably, identifying abnormalities for downstream analysis significantly reduces the computational demands of the system, and therefore significantly improves functionality of the system. As a result, implementation of this method improves the function of the text generation system, as well as the overall system in which the text generation system is implemented.

Referring to FIG. 2, for example, is a schematic representation of a system or workflow 200 for preprocessing of an image prior to text generation, where preprocessing can comprise one or more steps. One or more abnormality module or models are trained, configured, or selected to identify an abnormality in a segmented organ or region of interest. For example, an X-Y abnormality detection method such as a fully convolutional neural network among others is utilized at 220 to detect abnormalities in the segmented organ or region of interest. Then a Z abnormality detection method such as 2D CNN is utilized to localize the detected abnormality in three-dimensional space at 230.

At step 160 of the method, one or more features are extracted from the one or more identified abnormalities in the segmented organ or region of interest. The system may extract any features necessary for analysis. These features may depend, for example, upon the imaging modality, the downstream process utilizes for analysis and text generation, the needs of the clinician or technician, and/or a variety of other factors. The extracted features may be utilized immediately and/or may be stored for future analysis. A variety of extraction methods and techniques may be utilized to extract the one or more features from the identified abnormalities.

According to one embodiment, once an abnormality or similar region of interest is identified, a triplicate representation can be sent into a strong network with weights known to extract semantic features such as a fine-tuned InceptionV3. The triplicate representation could be 2D slices including three representation of the dynamic range and/or axial, coronal and sagittal cuts along x, y, z point of interest. This should be repeated for each abnormality candidate. To overcome issues with scale and various reconstruction algorithms, the system may also utilize dicom tags which describe the voxel size and algorithm and methods used. The feature vector generated from this process can then go to the text generating LSTM as described below.

Figure 3:
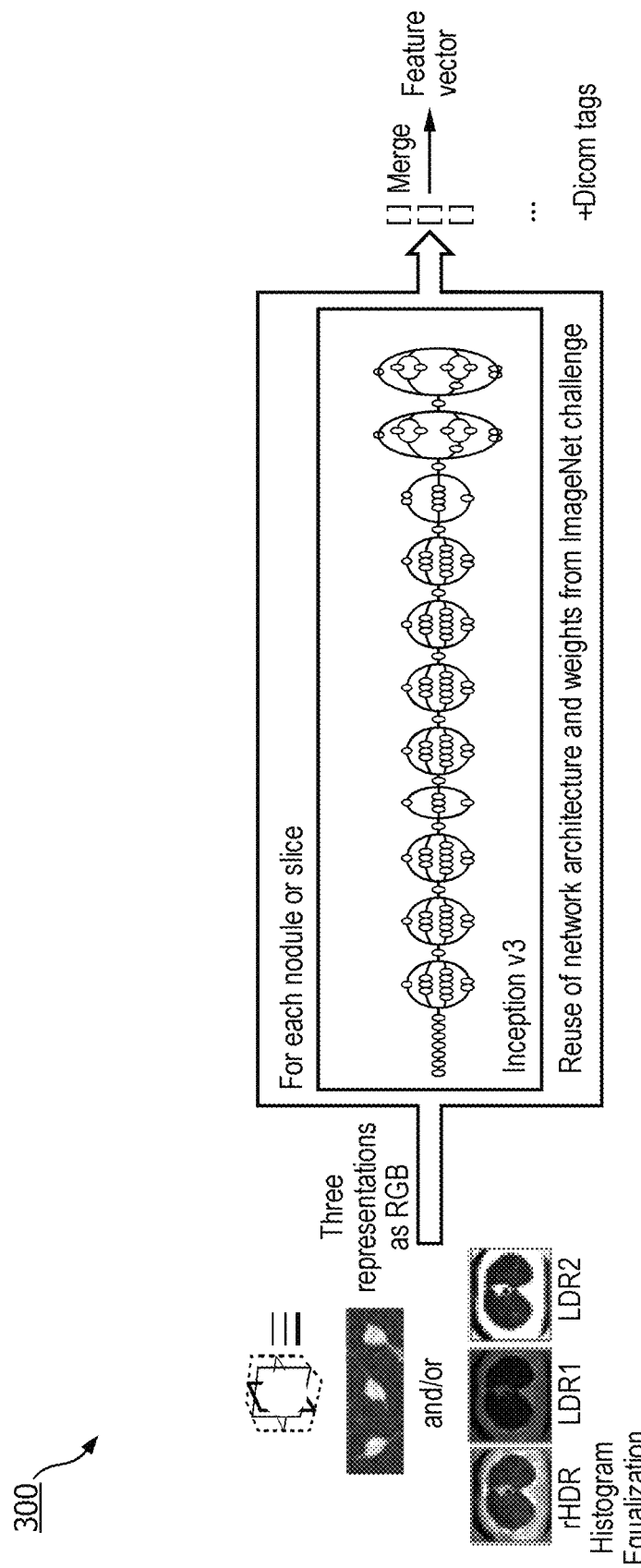
FIG. 3 is a schematic representation of a system or workflow for extracting features from a segmented image prior to text generation, in accordance with an embodiment.

Referring to FIG. 3, for example, is a schematic representation of a system or workflow 300 for extracting features from a segmented image prior to text generation. According to this embodiment, the identified abnormality is represented in three representations as RGB, and for each nodule or slice the abnormality is analyzed to extract one or more features. The extracted features can then be merged to generate a feature vector, with or without dicom tags. The feature vector can then be utilized by the text generation model.

At step 170 of the method, the system generates a textual description of the identified abnormality. According to an embodiment, a trained text generation model or module utilizes one or more extracted features and/or a feature vector generate the textual description of the identified abnormality. According to an embodiment, the trained text generation model or module utilizes a long short-term memory (LSTM) network which is trained as a language model conditioned on image encoding, although many other methods are possible.

Figure 4:
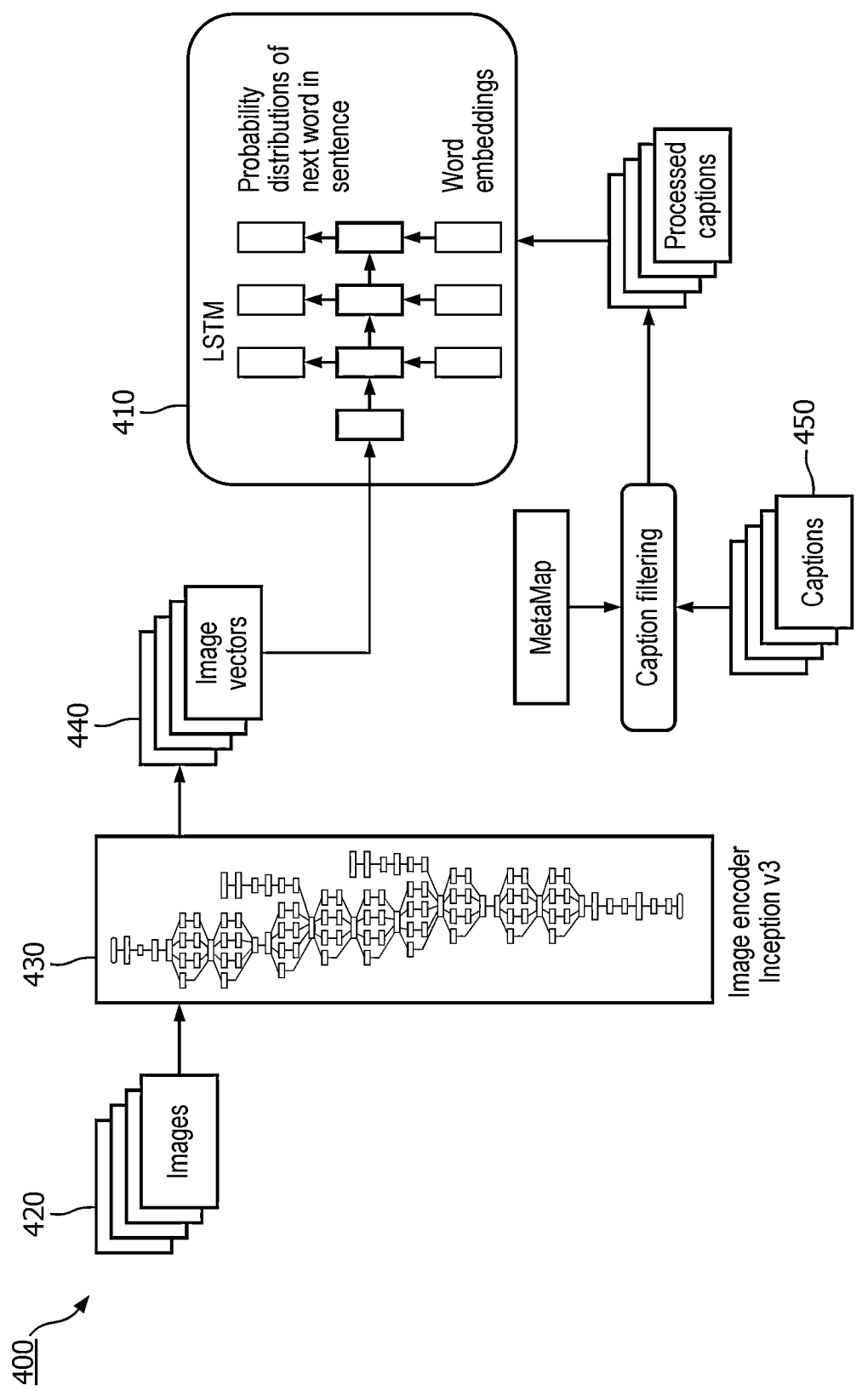
FIG. 4 is a schematic representation of a system or workflow for automated text generation, in accordance with an embodiment.

Referring to FIG. 4, in one embodiment, is a schematic representation of a system or workflow 400 for automated text generation. According to an embodiment, a text generation model or module 410 utilizes image vectors or features to generate a textual description. An image 420 is processed at 430 by the system, including one or more steps of the method described or envisioned herein, and image vectors or features 440 are generated from one or more identified abnormalities. These image vectors or features 440 are provided as input to the text generation model or module 410, which utilizes a long short-term memory (LSTM) network or similar process or method to generate a textual description of the abnormality in the image. The text generation model or module 410 is trained at 450, as described or otherwise envisioned herein, to automatically generate text from image vectors or features 440.

At optional step 172 of the method, the system combines generated textual description from two or more identified abnormalities into a single textual description. For example, in an endoscopy report the slices identified in various regions of the gastrointestinal regions—such as the esophagus, stomach, and duodenum—presenting mucosal erosion abnormalities can be combined into a single caption such as "mucosal erosions seen at multiple locations of upper GI." The text generation module or model can therefore be trained to receive as input a series of captions, identify any correlation and co-reference between the captions with respect to abnormalities using clinical NLP tools such as MetaMap with UMLS terminologies to come up with meaningful captions.

At step 180 of the method, the text generation system reports the generated textual description to a user via a user interface of the system. The generated textual description may be provided in any format to the user, who may be a technician, clinician, or other user of the system. For example, the generated textual description may be provided via a printed report, visual display, vocalization, digital download or upload, and/or via any other method of information communication. Accordingly, the user interface may comprise any component or method for information transmission, including but not limited to a printer, display, speaker, and/or any other component or element. The generated textual description may be provided together with other information such as the received medical image, metadata about the patient and/or the medical image, and/or any other information.

As an additional step 190 of the method, a technician, clinician, or other user receiving the generated textual description utilizes the description to inform a diagnosis, treatment, and/or any other aspect of medical diagnosis, care, or treatment. For example, a technician receiving the generated textual description can utilize the information to supplement or replace a visual inspection of the medical image. A clinician receiving the generated textual description can utilize the information to make or supplement a diagnosis or other clinical analysis, and/or can utilize the information to make or supplement a course of treatment for a patient.

Figure 5:
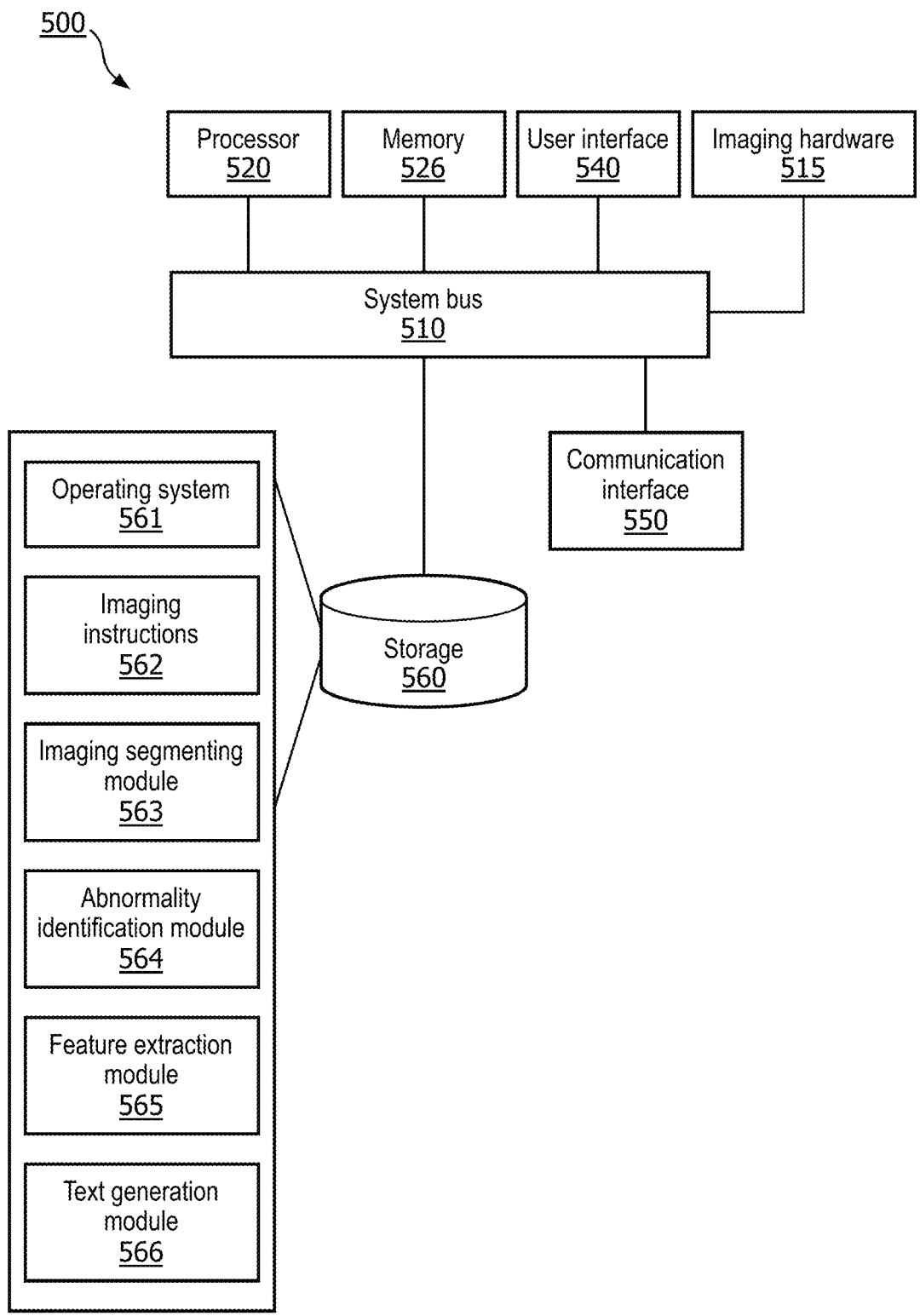
FIG. 5 is a schematic representation of modules for generating a textual description of a medical image inside a computer system architecture, in accordance with an embodiment.

Referring to FIG. 5, in one embodiment, is a schematic representation of a text generation system 500. System 500 can comprise any of the modules, elements, databases, processors, and/or other components described or otherwise envisioned herein. For example, the textual description generation system can comprise a processor having or in communication with an image segmenting module configured or programmed to segment one or more anatomical regions in a three-dimensional medical image, an abnormality identification module configured or programmed to identify any abnormalities in the segmented anatomical region, a feature extraction module configured or programmed to extract one or more features from identified abnormalities in a segmented anatomical region, and/or a text generation module configured to utilize or programmed with one or more text generation models to generate a textual description of the medical image using the extracted features. System 500 includes one or more of a processor 520, memory 526, user interface 540, communications interface 550, and storage 560, interconnected via one or more system buses 510. In some embodiments, such as those where the system comprises or implements a medical imager, the hardware may include or otherwise be in communication with imaging hardware 515. It will be understood that FIG. 5 constitutes, in some respects, an abstraction and that the actual organization of the components of the system 500 may be different and more complex than illustrated.

According to an embodiment, system 500 comprises a processor 520 capable of executing instructions stored in memory 526 or storage 560 or otherwise processing data. Processor 520 performs one or more steps of the method, and may comprise one or more of the modules described or otherwise envisioned herein. Processor 520 may be formed of one or multiple modules, and can comprise, for example, a memory. Processor 520 may take any suitable form, including but not limited to a microprocessor, microcontroller, multiple microcontrollers, circuitry, field programmable gate array (FPGA), application-specific integrated circuit (ASIC), a single processor, or plural processors.

Memory 526 can take any suitable form, including a non-volatile memory and/or RAM. The memory 526 may include various memories such as, for example L1, L2, or L3 cache or system memory. As such, the memory 526 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 500. It will be apparent that, in embodiments where the processor implements one or more of the functions described herein in hardware, the software described as corresponding to such functionality in other embodiments may be omitted.

User interface 540 may include one or more devices for enabling communication with a user such as an administrator, technician, or clinician. The user interface can be any device or system that allows information to be conveyed and/or received, and may include a display, a mouse, and/or a keyboard for receiving user commands. In some embodiments, user interface 540 may include a command line interface or graphical user interface that may be presented to a remote terminal via communication interface 550. The user interface may be located with one or more other components of the system, or may located remote from the system and in communication via a wired and/or wireless communications network.

Communication interface 550 may include one or more devices for enabling communication with other hardware devices. For example, communication interface 550 may include a network interface card (NIC) configured to communicate according to the Ethernet protocol. Additionally, communication interface 550 may implement a TCP/IP stack for communication according to the TCP/IP protocols. Various alternative or additional hardware or configurations for communication interface 550 will be apparent.

Storage 560 may include one or more machine-readable storage media such as read-only memory (ROM), random-access memory (RAM), magnetic disk storage media, optical storage media, flash-memory devices, or similar storage media. In various embodiments, storage 560 may store instructions for execution by processor 520 or data upon which processor 520 may operate. For example, storage 560 may store an operating system 561 for controlling various operations of system 500. Where system 500 implements imaging hardware 515, storage 560 may include imaging instructions 562 for operating the imaging hardware 515. Storage 560 may also comprise one or more of an image segmenting module 563, an abnormality identification module 564, a feature extraction module 565, a text generation module 566. The storage 560 may store additional software components required to execute the functionality described herein, which also may control operations of hardware 500.

It will be apparent that various information described as stored in storage 560 may be additionally or alternatively stored in memory 526. In this respect, memory 526 may also be considered to constitute a storage device and storage 560 may be considered a memory. Various other arrangements will be apparent. Further, memory 526 and storage 560 may both be considered to be non-transitory machine-readable media. As used herein, the term non-transitory will be understood to exclude transitory signals but to include all forms of storage, including both volatile and non-volatile memories.

While system 500 is shown as including one of each described component, the various components may be duplicated in various embodiments. For example, processor 520 may include multiple microprocessors that are configured to independently execute the methods described herein or are configured to perform steps or subroutines of the methods described herein such that the multiple processors cooperate to achieve the functionality described herein. Further, where system 500 is implemented in a cloud computing system, the various hardware components may belong to separate physical systems. For example, processor 520 may include a first processor in a first server and a second processor in a second server.

According to an embodiment, system 500 stores, utilizes, and/or otherwise comprises one or more modules to carry out one or more functions or steps of the methods described or otherwise envisioned herein. For example, system 500 may comprise an image segmenting module 563, an abnormality identification module 564, a feature extraction module 565, a text generation module 566. According to an embodiment, image segmenting module 563 is configured to analyze a received three-dimensional medical image to segment one or more anatomical regions from a remainder of the image. The segmentation module may use a programmed or trained segmentation model to perform organ segmentation with adaptive thresholding. The segmentation model or module may utilize thresholding or other analysis parameters to identify an organ or other region of interest relative to background or areas not of interest.

According to an embodiment, system 500 stores, utilizes, and/or otherwise comprises an abnormality identification module 564 configured, programmed, or trained to identify an abnormality in a segmented organ or region of interest. According to an embodiment an abnormality detection method, such as a convolutional neural network among other possible methods, is utilized to detect abnormalities in the segmented organ or region of interest. Additionally, an abnormality detection method such as 2D CNN or LSTM can be utilized to localize the detected abnormality in three-dimensional space.

According to an embodiment, system 500 stores, utilizes, and/or otherwise comprises a feature extraction module 565 configured, programmed, or trained to extract one or more features from the identified abnormalities in the segmented organ or region of interest. A wide variety of feature exaction methodologies or systems may be utilized. The extracted features may depend, for example, upon the imaging modality, the downstream process utilizes for analysis and text generation, the needs of the clinician or technician, and/or a variety of other factors. The extracted features may be utilized immediately and/or may be stored for future analysis. A variety of extraction methods and techniques may be utilized to extract the one or more features from the identified abnormalities. According to an embodiment, two or more extracted features are merged or otherwise combined to generate a feature vector. The extracted feature(s) and/or feature vector is utilized by the text generation module as described or otherwise envisioned herein.

According to an embodiment, system 500 stores, utilizes, and/or otherwise comprises a text generation module 566 trained or configured to generate a textual description of the medical image using the extracted features. According to an embodiment, text generation module 566 utilizes, implements, or comprises a trained text generation model to utilize one or more extracted features and/or a feature vector to generate a textual description of the identified abnormality. According to an embodiment, the trained text generation model or module utilizes a long short-term memory (LSTM) network which is trained as a language model conditioned on image encoding, although many other methods are possible. According to an embodiment, text generation module 566 combines generated textual description from two or more identified abnormalities into a single textual description.

According to an embodiment, the text generation systems and methods described or otherwise envisioned herein provide numerous advantages over the prior art. The functionality of a computer system implementing the text generation method is significantly improved, as the computer system is able to automatically generate descriptive text for a medical image in contrast to prior art systems. For example, there is improved patient care workflow due to the reduced time required for clinician documentation. There is also an increase in clinician productivity due to the automated imaging annotation and report generation. There is also improved automated curation of retrospective dataset for analytics, comparisons with similar cases, and clinical trials cohort creation. The methods and systems also support clinical decision making by providing a second reader, smart alerts for abnormalities of interest. Among other benefits this reduces clinician fatigue, particularly for complex and cognitively-expensive reads. The methods and systems also improve patient outcomes by reducing false-positives, lowering error rates, improving sensitivity, and preventing missed incidentals findings. These benefits improve, for example, patient and staff satisfaction which provides additional time for clinician-patient interactions.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for generating a textual description of a medical image, comprising:
  receiving the medical image and associated Digital Imaging and Communications in Medicine (DICOM) tags, the medical image comprising an anatomical region, the anatomical region comprising one or more abnormalities;

segmenting the anatomical region in the received medical image;

identifying at least one of the one or more abnormalities in the segmented anatomical region;

extracting one or more features from the identified at least one of the one or more abnormalities using the DICOM tags;

generating, using the extracted features and a trained text generation model, the textual description of the identified at least one of the one or more abnormalities, wherein the textual description includes a description of a physical feature of the at least one of the one or more abnormalities; and reporting, via a user interface, the generated textual description of the identified at least one of the one or more abnormalities to assist a user with evaluating the medical image.

2. The method of claim 1, wherein the medical image is a three-dimensional image.

3. The method of claim 1, wherein identifying the at least one of the one or more abnormalities in the segmented anatomical region further comprises localizing the identified at least one of the one or more abnormalities in three-dimensional space.

4. The method of claim 1, further comprising a step of combining the generated textual descriptions for two or more of the identified at least one of the one or more abnormalities into a single textual description.

5. The method of claim 4, wherein the two or more identified abnormalities are combined into the single textual description by:

receiving, with the trained text generation model, a series of captions as input;

identifying, with the trained text generation model, a correlation or co-reference between captions with respect to the two or more identified abnormalities using a clinical natural language processor; and generating the single textual description with a single caption that describes the two or more identified abnormalities.

6. The method of claim 5, wherein the single textual description includes a description of an abnormality feature that is common to the two or more abnormalities, each of the two or more abnormalities corresponding to a different anatomical organ or tissue of a particular physiological system.

7. The method of claim 1, wherein two or more extracted features are merged to generate a feature vector for the identified at least one of the one or more abnormalities.

8. The method of claim 1, further comprising a step of training, using a training data set, the text generation model to generate the textual description from an identified abnormality of the identified at least one of the one or more abnormalities.

9. The method of claim 1, wherein the step of identifying the at least one of the one or more abnormalities in the segmented anatomical region comprises employing a convolutional neural network, a long short-term memory (LSTM) network, or the convolutional neural network and the LSTM network.

10. The method of claim 1, wherein the step of generating the textual description of the identified at least one of the one or more abnormalities comprises employing a long short-term memory (LSTM) network.

11. The method of claim 1, further comprising: training the trained text generation model, including, utilizing an attention mechanism over image features in a decoder, to learn inherent alignments of caption words for image regions without segmentation information.

12. The method of claim 1, further comprising: training the trained text generation model using descriptive sentences from medical literature in view of features extracted from medical images.

13. The system of claim 1, further comprising:

encoding the one or more features into a fixed-length vector representation; and decoding the representation into a natural language description to produce the textual description.

14. A system for generating a textual description of a medical image, comprising:

an image segmenting module configured to receive the medical image, the medical image comprising an anatomical region, the anatomical region comprising one or more abnormalities, and further configured to segment the anatomical region in the received medical image;

an abnormality identification module configured to identify at least one of the one or more abnormalities in the segmented anatomical region;

a feature extraction module configured to extract one or more features from the identified at least one of the one or more abnormalities using DICOM tags;

a text generation module configured to generate, using the extracted features and a trained text generation model, a textual description of a physical characteristic of the identified at least one of the one or more abnormalities; and a user interface configured to report the generated textual description.

15. The system of claim 14, wherein the medical image is a three-dimensional image.

16. The system of claim 14, wherein the feature extraction module is configured to combine two or more extracted features to generate a feature vector for the identified at least one of the one or more abnormalities.

17. The system of claim 14, wherein the text generation module is configured to combine the generated textual descriptions for two or more of the identified at least one of the one or more abnormalities into a single textual description.

18. The system of claim 14, wherein the text generation module is configured to be trained, using a training data set, to generate the textual description from the identified at least one of the one or more abnormalities.

19. The system of claim 14, further comprising: training the trained text generation model, including learning probabilities of a word given an input word and a training medical image, to produce a model capable of generating a phrase or sentence in response to the medical image.

20. The system of claim 14, wherein the textual description of the identified at least one of the one or more abnormalities describes a physical feature of a surface abnormality of anatomical tissue in the segmented anatomical region.

21. A non-transitory computer readable medium storing instructions executable by at least one processor for performing a method comprising the steps of:

receiving a medical image and associated Digital Imaging and Communications in Medicine (DICOM) tags, the medical image comprising an anatomical region, the anatomical region comprising one or more abnormalities;

segmenting the anatomical region in the received medical image;

identifying at least one of the one or more abnormalities in the segmented anatomical region;

extracting one or more features from the identified at least one of the one or more abnormalities using the DICOM tags;

generating, using the extracted features and a trained text generation model, the textual description of the identified at least one of the one or more abnormalities, wherein the textual description includes at least a description of a physical feature of the at least one of the one or more abnormalities; and reporting, via a user interface, the generated textual description of the identified at least one of the one or more abnormalities.

\* \* \* \* \*